(12) United States Patent
He et al.

(10) Patent No.: US 6,895,177 B2
(45) Date of Patent: May 17, 2005

(54) VAPOR DISPENSING DEVICE HAVING IMPROVED TRANSVERSE LOADING STABILITY

(75) Inventors: Mengtao Pete He, Scottsdale, AZ (US);
Carl Triplett, Scottsdale, AZ (US);
Mary J. Conway, Phoenix, AZ (US);
David Rinaldis, Longmont, CO (US);
Michael Strasser, Boulder, CO (US);
Francis Joseph Mills, IV, Munich (DE)

(73) Assignee: The Dial Corporation, Scottsdale, AZ (US)

(*) Notice: Subject to any disclaimer, the term of this patent is extended or adjusted under 35 U.S.C. 154(b) by 0 days.

(21) Appl. No.: 10/222,070

(22) Filed: Aug. 16, 2002

(65) Prior Publication Data

US 2004/0033064 A1 Feb. 19, 2004

(51) Int. Cl.[7] .................................. F24F 6/00
(52) U.S. Cl. ........................ 392/392; 392/390
(58) Field of Search ................. 392/386, 390, 392/392, 394, 395; 239/34, 35, 135, 136; 261/DIG. 65, 141, 142

(56) References Cited

U.S. PATENT DOCUMENTS

| | | |
|---|---|---|
| 4,518,212 A | 5/1985 | Rumble |
| 4,530,556 A | 7/1985 | Bonus |
| 4,731,520 A | 3/1988 | Glucksman et al. |
| 4,795,883 A | 1/1989 | Glucksman et al. |
| 4,804,821 A * | 2/1989 | Glucksman ............. 392/390 |
| 4,849,606 A | 7/1989 | Martens, III et al. |
| 4,886,469 A | 12/1989 | Jseng |
| 5,004,435 A | 4/1991 | Jammet |
| 5,106,317 A | 4/1992 | Taylor |
| 5,111,477 A | 5/1992 | Muderlak |
| 5,136,684 A | 8/1992 | Lonker et al. |
| 5,295,845 A | 3/1994 | Changxing |
| 5,375,728 A | 12/1994 | West |
| 5,402,517 A | 3/1995 | Gillett et al. |
| 5,522,008 A | 5/1996 | Bernard |
| 5,574,821 A | 11/1996 | Babasade |
| 5,647,052 A | 7/1997 | Patel et al. |
| 5,664,958 A | 9/1997 | Chadwick et al. |
| 5,937,140 A | 8/1999 | Leonard et al. |
| 5,955,701 A | 9/1999 | Schockner et al. |
| 5,976,503 A | 11/1999 | Martin et al. |
| 6,044,202 A | 3/2000 | Junkel |
| 6,097,881 A | 8/2000 | DeWitt et al. |
| 6,104,867 A | 8/2000 | Stathakis et al. |
| 6,123,935 A | 9/2000 | Wefler et al. |
| 6,141,496 A | 10/2000 | Sundberg et al. |
| 6,289,176 B1 | 9/2001 | Martter et al. |
| 2001/0053283 A1 | 12/2001 | Levine et al. |
| 2003/0152374 A1 * | 8/2003 | Grone et al. ............. 392/392 |

OTHER PUBLICATIONS

Brochure–"Decora Devices," by Leviton, date unknown, Section A, pps. A1–A36.

* cited by examiner

*Primary Examiner*—Sang Paik
(74) *Attorney, Agent, or Firm*—Snell & Wilmer LLP

(57) ABSTRACT

A vapor dispensing device having a high transverse loading stability includes a relatively low profile with respect to the supporting wall or electrical receptacle such that the frequency and impact of accidental physical contact with the device are appropriately reduced. To achieve a low profile, the housing of a vapor dispensing device is designed such that the distance from the outlet face of the wall receptacle to a worst-case transverse loading point ($d_L$) is less than the distance from the plug to a worst-case support point ($d_S$).

3 Claims, 6 Drawing Sheets

VAPOR DISPENSING DEVICE HAVING IMPROVED TRANSVERSE LOADING STABILITY

FIELD OF INVENTION

This invention generally relates to vapor dispensing devices such as air fresheners. More particularly, the invention relates to electrically-powered vapor dispensing devices.

BACKGROUND OF THE INVENTION

Electrically-operated vapor dispensing devices have been used for several years and have become common household products. These devices are typically inserted into a conventional electrical receptacle to obtain electricity for heating a perfumed fluid, wax, paraffin, or other fuel to produce a pleasing aroma that is dispersed within a room or other confined space. Examples of electric vapor dispensers include the RENUZIT products available from The Dial Corporation of Scottsdale, Ariz. One such product is shown in U.S. Design Pat. Ser. No. D449,101 which issued on Oct. 9, 2001 to Wolpert et al.

Many conventional vapor dispensing devices exhibit a marked disadvantage, however, in that the size of the dispenser housing frequently extends outwardly from the wall receptacle for a significant distance. Because of this distance, an outcropping from the wall is produced that can become bumped, jostled or otherwise accidentally placed into contact with people or objects. Such contact may have the effect of pushing the dispenser out of the wall receptacle, and may potentially break or deform the device. Accordingly, it is desirable to produce an electric vapor dispenser that is resilient to accidental contact that may produce breakage or displacement of the dispenser.

SUMMARY OF THE INVENTION

A vapor dispensing device having a high transverse loading stability is provided in accordance with various embodiments of the invention. Such a device includes a relatively low profile with respect to the supporting wall or electrical receptacle such that the frequency and impact of accidental physical contact with the device are appropriately reduced. According to an exemplary embodiment, the housing of a vapor dispensing device is designed such that the perpendicular distance from the outlet face of the wall receptacle to a worst-case transverse loading point ($d_L$) is less than the distance from the plug to a worst-case support point ($d_S$) such that a transverse loading coefficient $\eta = d_S/d_L$ is greater than one. These and other aspects of the invention shall become more apparent when read in conjunction with the accompanying drawing figures and the attached detailed description of exemplary embodiments.

BRIEF DESCRIPTION OF THE DRAWINGS FIGURES

The features and advantages of the present invention are hereinafter described in the following detailed description of exemplary embodiments to be read in conjunction with the accompanying drawing figures, wherein like reference numerals are used to identify the same or similar parts in the similar views, and:

DETAILED DESCRIPTION OF EXEMPLARY EMBODIMENTS

Figure 1:
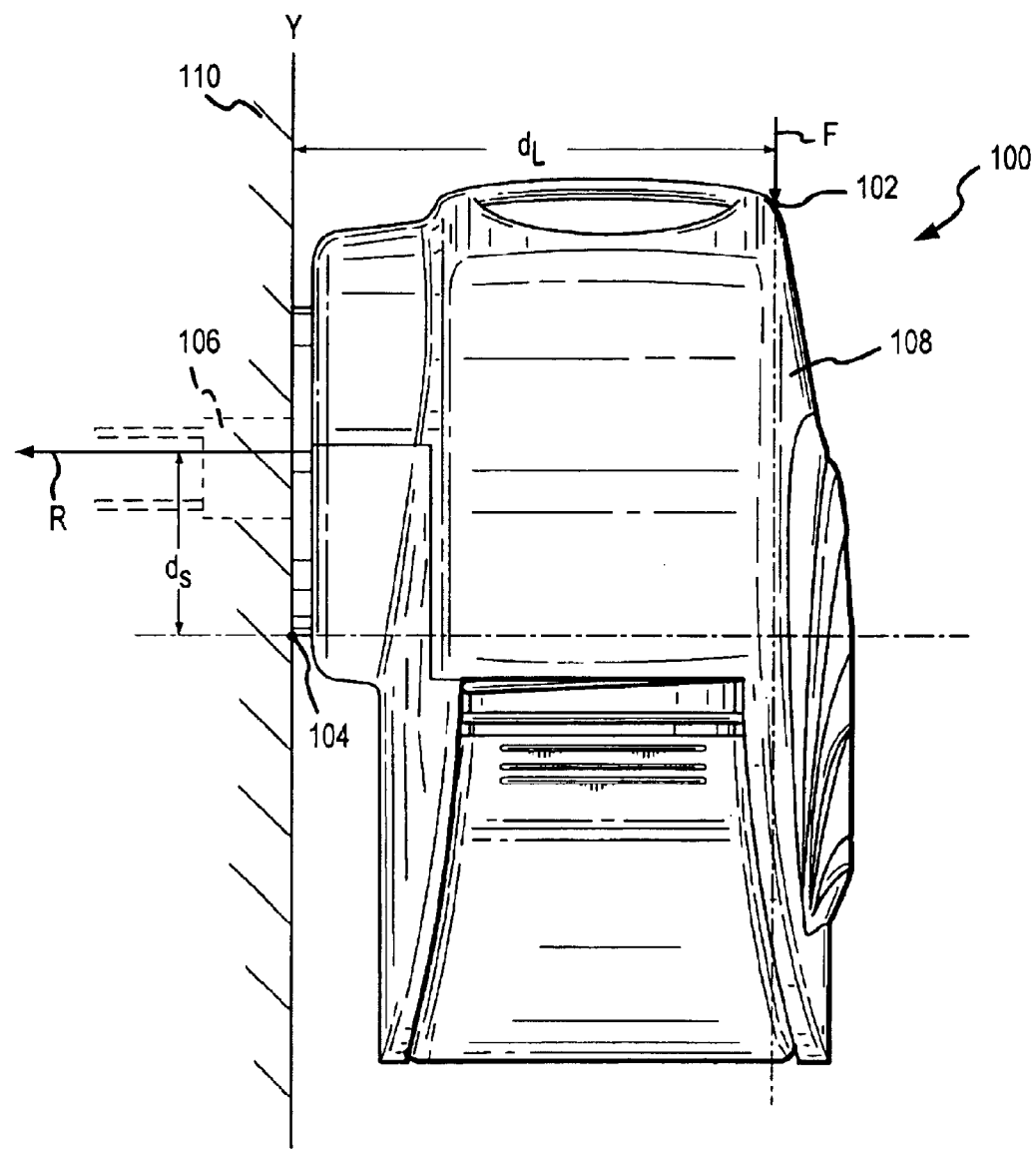
FIG. 1 is a side view of a conventional vapor dispensing device.

With reference to FIG. 1, a conventional vapor dispensing device 100 typically includes a housing 108 coupled to a plug 106 that is capable of being inserted into a conventional electrical receptacle in a wall or other structure 110. Housing 108 typically retains a vapor-producing material such as a perfumed fluid, wax, paraffin or the like that can be combusted, electrolyzed or otherwise processed by a resistance heater or other appropriate device to produce a vapor that can be dispersed through a room, vehicle or other confined space.

Due to the relatively large profile of vapor dispensing device 100 with respect to wall 110, however, forces impacting on the vapor dispensing device 100 suitably produce rotational moments about a support point along the wall. For example, force F applied at point 102 on housing 108 suitably produces a rotational moment about point 104 that is equal to the magnitude of force F multiplied by the distance $d_L$ from the effective point of force F to the front face of the outlet. This loading distance $d_L$ is defined as the distance from the effective point of force F from an axis that is perpendicular to the front face of the outlet and that runs through a support point 104. In the vapor-dispensing device 100 shown in FIG. 1, support point 104 is the point on device 100 that bears the greatest impact of force F.

Application of force F produces a reactive force R between plug 106 and wall 110. Reactive force R appropriately maintains vapor-producing device 100 in contact with the outlet receptacle, and produces a counter-balancing rotational moment upon support point 104. The moment produced by the stabilizing force R about support point 104 is equal to the magnitude of reactive force R multiplied by the distance from force R to support point 104. This distance is referred to herein as support distance $d_S$ and is typically measured along an axis parallel to the outlet face. Because vapor dispensing device 100 remains rigidly fixed in position and does not move in response to the application of force F, the sum of the moments about point 104 suitably equates to zero. The sum of the moments about point 104 may therefore be expressed as:

$$R\, d_S - F\, d_L = 0 \qquad \text{(Equation 1)}$$

Manipulating these terms algebraically shows that the resulting force R produced into the wall by force F is as follows:

$$R = F\frac{d_L}{d_S} = \frac{F}{\eta} \qquad \text{(Equation 2)}$$

wherein $\eta$ is a transverse loading coefficient defined as the ratio of the support distance $d_S$ to the load distance $d_L$. In vapor dispensing device 100 shown in FIG. 1, it is clear that lateral distance $d_L$ is relatively large compared to $d_S$, thereby indicating that the transverse loading coefficient $\eta$ is less than 1. Accordingly, it can be readily shown from Equation 2 that a load force F upon point 102 effectively produces a resultant force R that has a greater magnitude than that of force F when the transverse loading coefficient $\eta$ is less than one.

Figure 2:
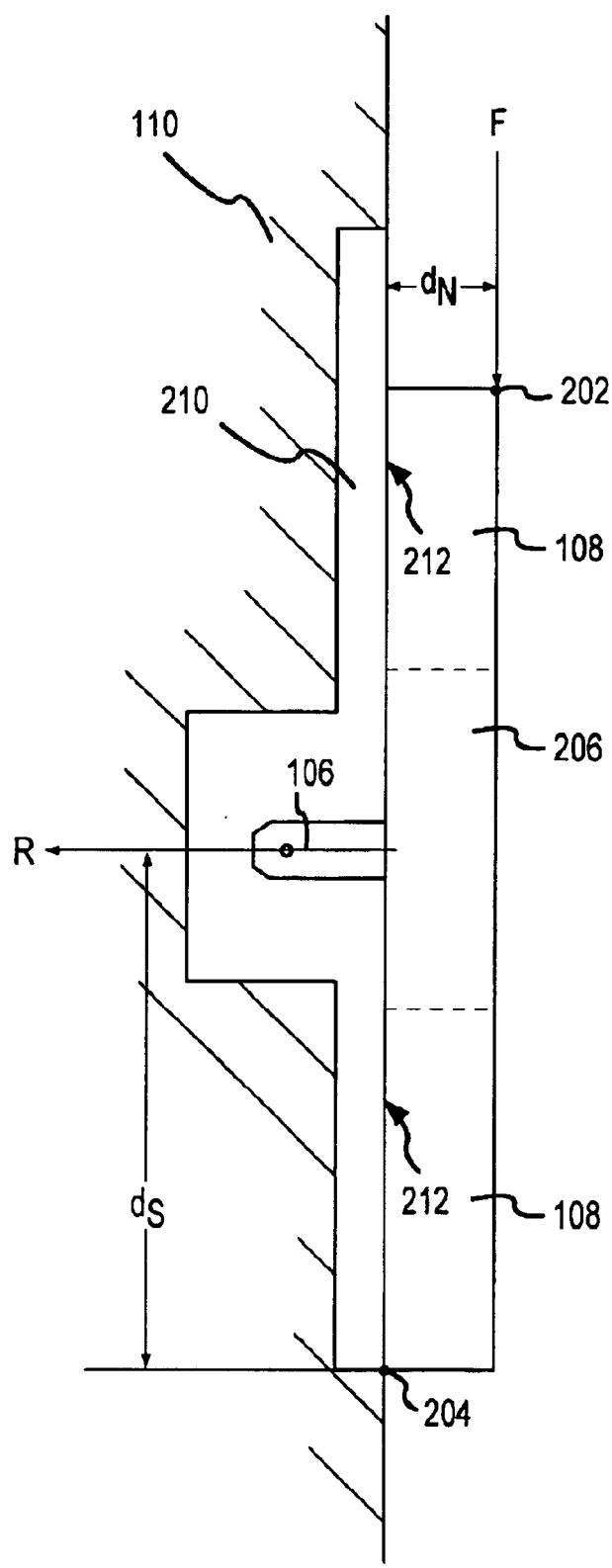
FIG. 2 is a side view of an exemplary vapor dispensing device with a high transverse loading stability.

FIG. 2 is a side view of a vapor dispensing device having an improved transverse loading stability. With reference now to FIG. 2, a vapor dispensing device 200 suitably includes a housing 108 coupled to a plug 106 that is capable of being inserted into the outlet face 212 of a conventional electrical receptacle 210 housed in a wall or other surface 110. Housing 108 may also include a conventional device outlet 206 electrically coupled to the plug that provides electrical power from plug 106 to a light or other electrically-powered device such as a hairdryer, curling iron, electric razor, kitchen appliance, or the like.

FIG. 2 depicts a force F impinging upon a worst-case transverse loading point 202 along housing 108. Worst-case loading point 202 is any point along the edge of device 200 that is furthest from the outer face 212 of the electrical receptacle. Worst-case loading point 202 corresponds to locations on housing 108 where the impinging force produces a maximum rotational moment about a worst-case support point 204, which is defined as the points on housing 108 wherein the moment produced by reactive force R is maximized. Worst-case support points 204 typically reside on an edge of housing 108 that is in physical contact with the front face of the receptacle and that is on a side of housing 108 opposite plug 106 from the impinging point of the force F. Accordingly, device 200 may exhibit multiple worst-case support points along an edge of housing 108 that provide equal reactive moments to external forces. Similarly, forces impinging upon each point along certain edges of housing 108 may produce identical moments in the various support points. Accordingly, the precise locations of worst-case loading and support points on device 400 vary widely depending upon the particular embodiment and forces applied.

In the device shown in FIG. 2, worst-case support point 204 is defined near the bottom of vapor dispensing device 200 at the point on housing 108 that bears the greatest loads from applied external forces. Worst-case transverse loading point 202 corresponds to the point on vapor dispensing device 200 whereupon application of a force F produces the greatest resultant force R between plug 106 and the surrounding receptacle 210. Using Equation 2 above, the resultant force R is:

$$R = Fd_L/d_S = \frac{F}{\eta}$$

In this case, however, the transverse loading coefficient $\eta$ is greater than one because support distance $d_S$ from plug 106 to support point 204 along outlet face 212 is designed to be greater than the lateral distance $d_L$ from outlet face 212 to loading point 202. Correspondingly, then, force F applied at worst-case transverse loading point 202 produces a resulting force R with a magnitude that is less than the magnitude of force F, thereby reducing the impact of force F on plug 106 and improving the overall transverse loading stability of vapor dispensing device 200.

Figure 3:
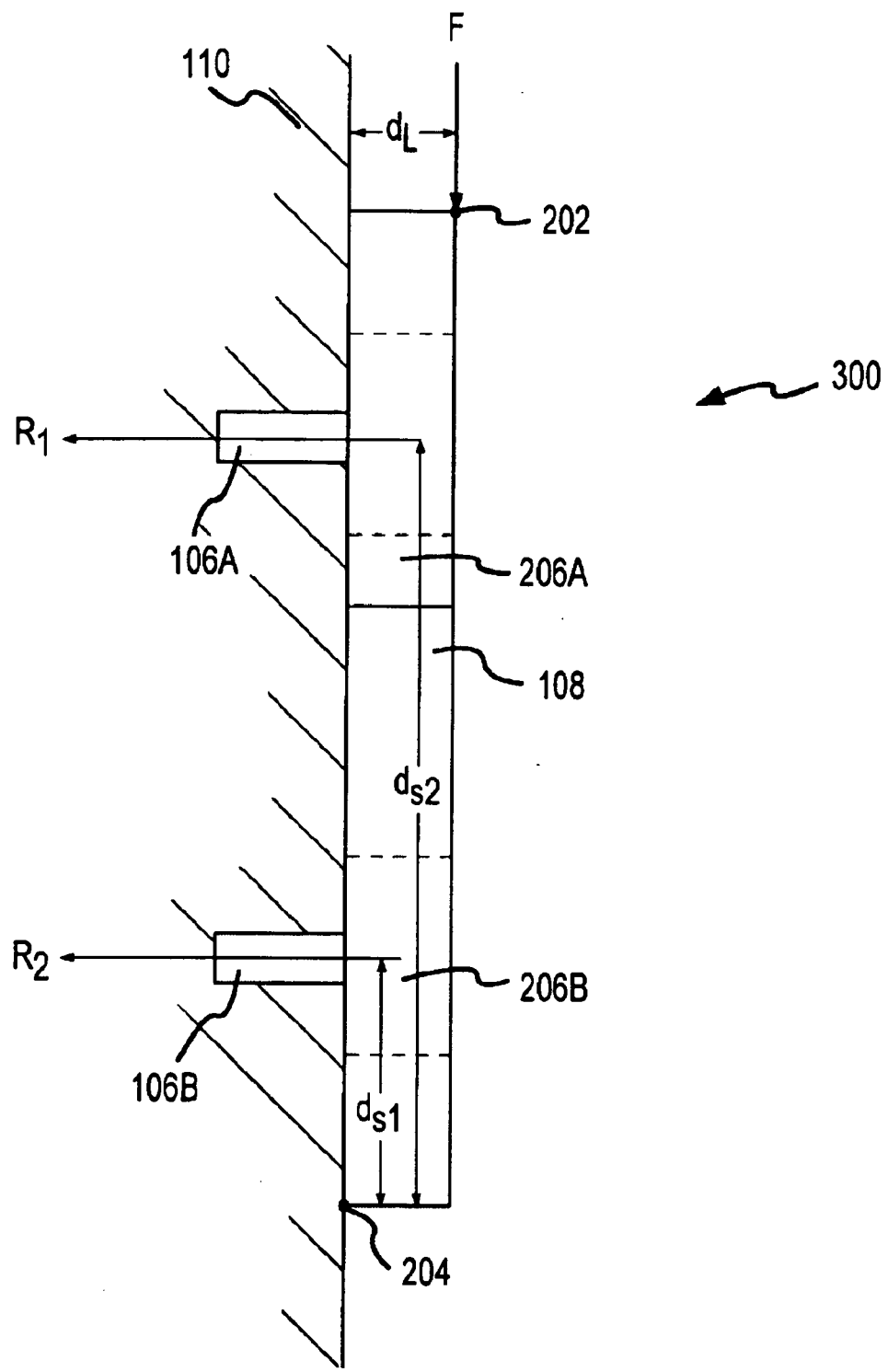
FIG. 3 is a side view of an exemplary vapor dispensing device having two plugs and a high transverse loading stability.

FIG. 3 is a side view of a vapor dispensing device having more than one plug which can be inserted into an electrical receptacle. With reference now to FIG. 3, a vapor dispensing device 300 suitably includes housing 108 coupled to two plugs 106a and 106b. Either or both of the plugs 106a–b may be an electrical communication with one or more device outlets 206 to provide electrical power from receptacle 210 (FIG. 2) to external devices such as lamps, hair dryers or the like.

In the embodiment shown, the worst-case transverse loading point remains at point 202, which is the greatest perpendicular distance $d_L$ from the face of the outlet. Similarly, worst-case support point 204 remains at the edge of housing 108 at a distance furthest from plugs 106A–B and opposite worst-case transverse loading point 202. Because two plugs 106A–B are provided, two resultant forces $R_1$ and $R_2$ are produced. Accordingly, the rotational moments about point 204 are appropriately expressed as:

$$R_1\ d_{S2} + R_2\ d_{S1} - F\ d_L = 0. \quad \text{(Equation 3)}$$

Algebraically manipulating Equation 3 results in:

$$F = R_1\ d_{S1}/d_L + R_2\ d_{S2}/d_L = R_1\ \eta_1 + R_2\ \eta_2 \quad \text{(Equation 4)}$$

wherein $\eta_1 = d_{S1}/d_L$ and $\eta_2 = d_{S2}/d_L$. Evaluating Equation 4 shows that force F applied at point 202 is appropriately counterbalanced by two resultant forces $R_1$ and $R_2$. In each case, the transverse loading coefficients $\eta_1$ and $\eta_2$ are designed to be greater than one such that the support distance $d_S$ is greater than the loading distance $d_L$ for each plug 106A–B. Because $R_1$ and $R_2$ are inversely proportional to $\eta_1$ and $\eta_2$, respectively, it may be readily shown that relatively large values for $\eta_1$ and $\eta_2$ result in correspondingly smaller reactive forces $R_1$ and $R_2$ for a constant value of F. Further, because unusually high values of $R_1$ and $R_2$ can cause breakage or movement of device 300, higher values for $\eta_1$ and $\eta_2$ thereby allow device 300 to produce lower reactive forces and to thereby withstand greater forces F without breakage or movement. Accordingly, the transverse loading stability of device 300 is improved.

FIGS. 4A–D are top, front, side and perspective views, respectively, of another exemplary embodiment of a vapor-dispensing device. With reference to FIGS. 4A–D, vapor dispensing device 400 suitably includes a housing 108 connecting to one or more plugs 106A–B. Housing 108 and plugs 106A–B are appropriately configured to correspond with the front face 212 of a wall-mounted outlet receptacle 210 (FIG. 4D) to provide device stability and electrical power.

Figure 4A:
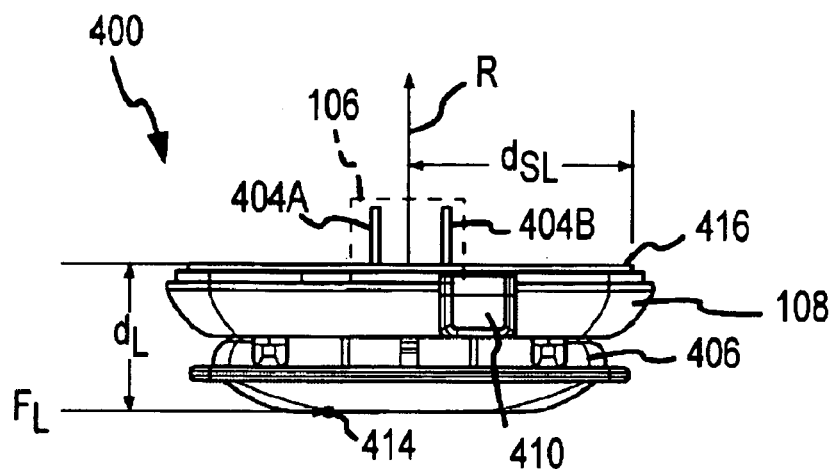
FIGS. 4A–D are top, front, side and perspective views, respectively, of an exemplary vapor dispensing device having a high transverse loading stability.
Figure 4B:
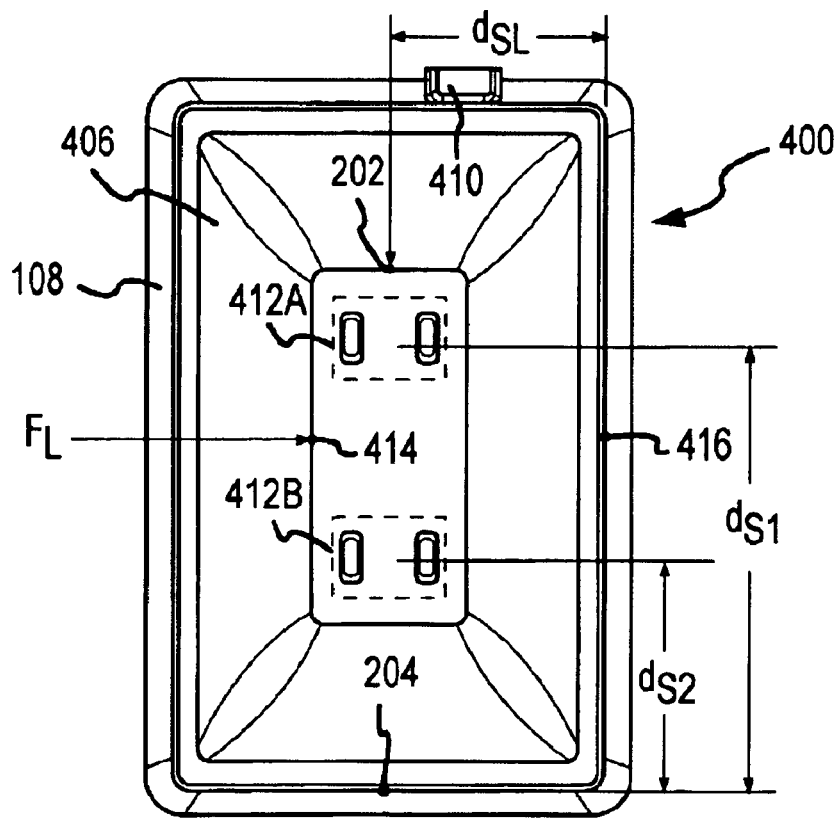

In the exemplary embodiment shown in the drawings, housing 108 suitably includes two optional device outlets 412A–B that allow the user to connect other appliances to plugs 106A–B to obtain electrical power while device 400 remains in use. Each of the plugs 106A–B has two prongs 404A–B as best seen in FIG. 4A. To simplify the discussion below, however, the reactive forces produced by each prong 404A–B are analyzed as a combined reactive force R for the entire plug 106. Plug 106 may conform to any electrical convention such as the 60 Hertz, 110 Volt alternating-current standard commonly used in North America. Alternatively, plug 106 may be configured to operate using direct current (e.g. current supplied by a battery) or any other electrical convention.

Fragrance is produced in device 400 by any conventional technique and structure. In an exemplary embodiment, device 400 suitably uses electrical resistance to heat a fragrance-producing fuel such as a perfumed fluid, wax or other substance maintained in a reservoir within or coupled to housing 108. In a further exemplary embodiment, device 400 suitably interfaces to an optional replaceable fragrance cartridge 406 to replenish the supply of fuel as needed. The cartridge may be discarded and replaced when the fuel is spent, when the user desires an alternate fragrance or as otherwise appropriate. An optional flat lamp, night light or other lighting feature may also be provided within fragrance-producing device 400. The term "housing" as used herein is intended to broadly include features such as removable cartridges, lamps and the like that may be coupled or otherwise attached to device 400.

Housing 108 may also include or interface with an optional fragrance intensity slider 410. Slider 410 allows users to adjust the intensity of fragrance produced by device 400 by moving slider 410 to a desired linear position corresponding to the rate by which fragrance is allowed to diffuse or move into the surrounding space. Alternate embodiments may use a rotary dial, switch or other control in place of slider 410 to adjust the fragrance intensity, or may eliminate fragrance intensity adjustment altogether.

Figure 4C:
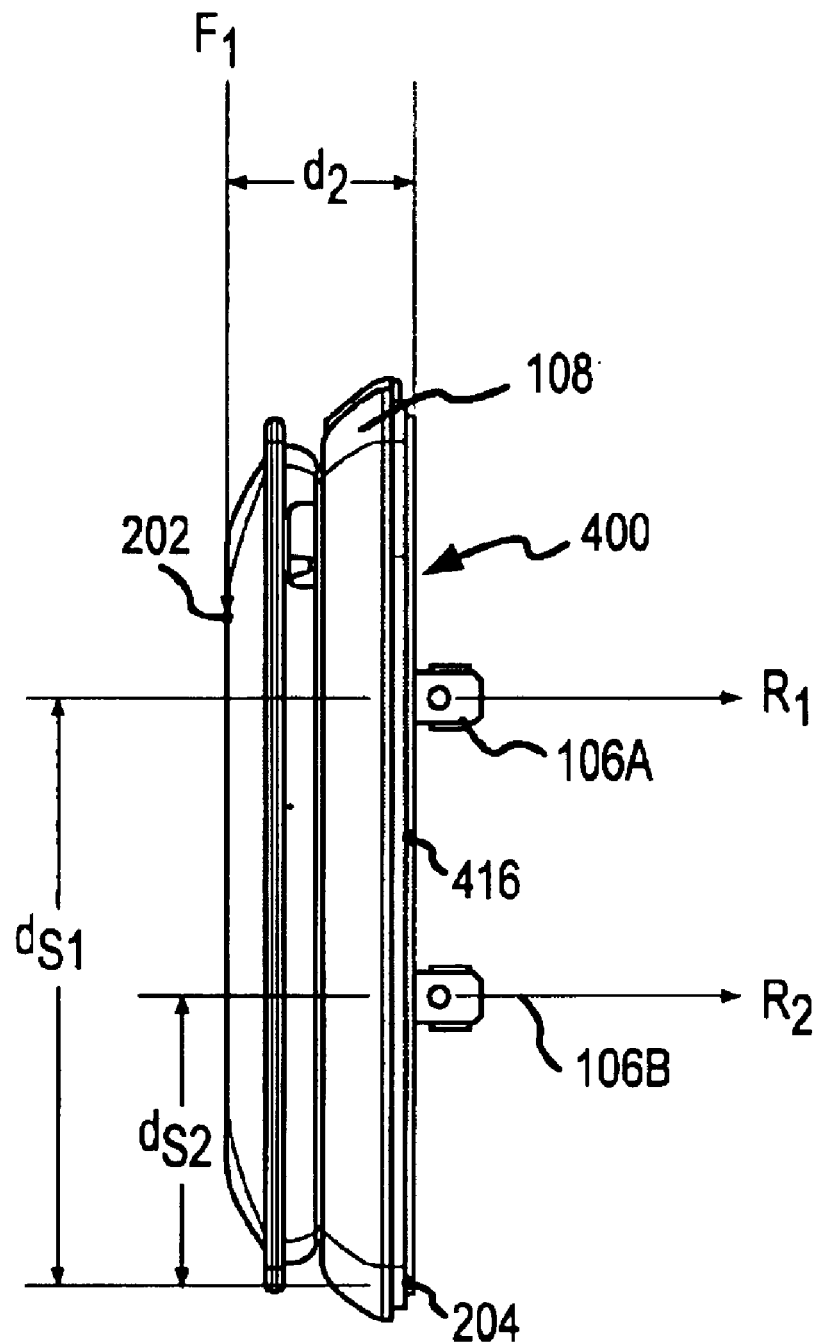
Figure 4D:
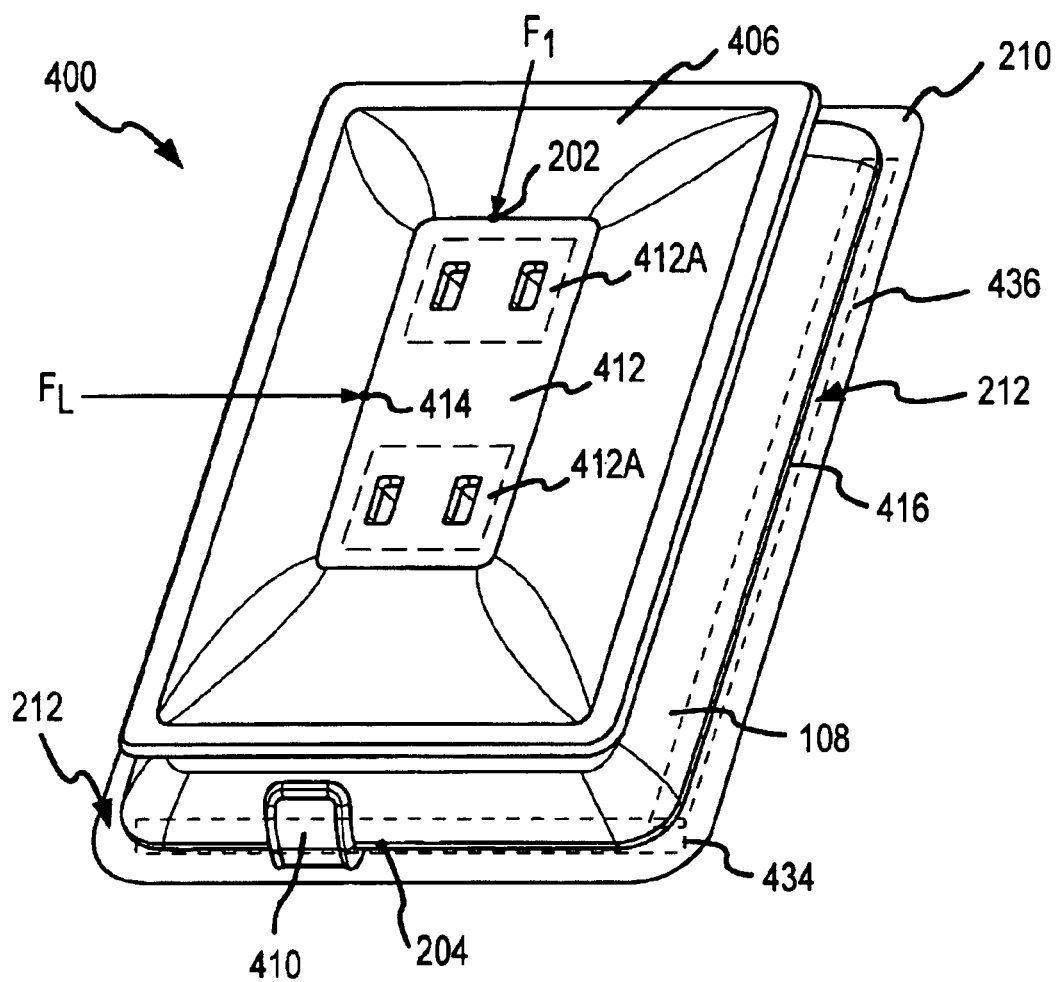

FIGS. 4A–D depict two separate forces $F_1$ and $F_L$ impinging upon worst-case transverse loading points 202 and 414, respectively. Worst-case loading points 202 and 414 correspond to locations on housing 108 where the impinging forces $F_1$ and $F_L$ produce maximum rotational moments upon device 400. Accordingly, the worst case loading points on device 400 are the points furthest from the outlet face along outer ridge 432 of device 400 as shown in FIG. 4D.

Worst case support points 204 and 416 lie along the outer edge of housing 108 facing the electrical receptacle and opposite plugs 106A–B, since the rotational moments produced by reactive forces $R_1$ and $R_2$ are maximized along edges 434 and 436 (FIG. 4D), respectively. To simplify discussion, points 204 and 416 are considered as worst case support points for forces $F_1$ and $F_L$, respectively, although other points along edges 434 or 436 would produce similar results.

With continued to FIGS. 4A–D, force $F_1$ is shown applied to worst-case loading point 202, which is located along the upper edge of housing 108 at a point furthest outward from the outlet face. Force $F_1$ is therefore applied a distance of $d_L$ (FIGS. 4A and 4C) from the outlet face to produce a moment of magnitude $F \times d_L$ about worst case support point 204. Plugs 106A and 106B effectively produce reactive forces $R_1$ and $R_2$ at distances $d_S$, and $d_{S2}$ from support point 204, respectively, to generate rotational moments about point 204 equal to $R_1 \times d_{S1}$ and $R_2 \times d_{S2}$, respectively. Applying the analysis of equation 4 set forth above, the transverse loading stability of device 400 is suitably improved by designing distances $d_{S1}$ and $d_{S2}$ to be relatively long compared to distance $d_L$. Stated another way, stability is improved by designing the maximum thickness of device 400 to be less than the shortest distance from either plug 106A–B to any loading edge (e.g. edges 434 and 436) of housing 108 that is in contact with outlet face 212.

Similarly, force $F_L$ is shown applied to worst-case loading point 414, which (like point 202) is located along the upper edge of housing 108 at a point furthest outward from the outlet face. Force $F_L$ is therefore applied a distance of $d_L$ (FIGS. 4A and 4C) from the outlet face to produce a moment of magnitude $F_L \times d_L$ about worst case support point 204, which lies along edge 436 as described above. Plugs 106A and 106B effectively produce reactive forces $R_1$ and $R_2$ at a distance $d_{SL}$ from support point 204. In this case, $R_1$ and $R_2$ are produced at an equal distance from support point 204 along an axis parallel to the outlet face as best seen in FIG. 4C. Accordingly, $R_1$ and $R_2$ generate rotational moments about point 204 with magnitudes equal to $R_1 \times d_{SL}$ and $R_2 \times d_{SL}$, respectively. Again applying the analysis of equation 4 set forth above, the transverse loading stability of device 400 is suitably improved by designing distance $d_{SL}$ to be relatively long compared to distance $d_L$.

For the sake of brevity, conventional electrical and mechanical design techniques used in developing various vapor-dispensing devices (and the various components thereof) are not described in detail herein. Accordingly, devices disclosed herein may be readily modified to create equivalent embodiments through application of general electrical and mechanical principles. Although the embodiments described herein show vapor dispensing devices that are generally quadrilateral in shape, for example, other design styles could be formulated. Vapor dispensing devices could be readily formulated with angular, round, oval or other shapes, for example, as well as with combinations of multiple shapes and structures. In a further embodiment, the vapor dispensing device may be adorned with an ornamental design such as a floral design, an outdoor scene, a cartoon or movie character, or the like. Moreover, the general concepts of improving transverse loading stability described herein may be applied to other electrical devices such as air filters, nightlights, audio speakers, wireless control devices, timers and the like.

The particular implementations shown and described herein are examples of the invention and are not intended to otherwise limit the scope of the invention in any way. The connecting lines shown in the various figures contained herein are intended to represent exemplary functional relationships and/or physical couplings between the various elements. It should be noted that many alternative or additional functional relationships, physical connections or logical connections may be present in a practical vapor-dispensing device. The corresponding structures, materials, acts and equivalents of all elements in the claims below are intended to include any structure, material or acts for performing the functions in combination with other claimed elements as specifically claimed. The scope of the invention should be determined by the appended claims and their legal equivalents, rather than by the examples given above. No item or component is essential to the practice of the invention unless the element is specifically described herein as "critical", "essential" or "required".

What is claimed is:

1. A vapor dispensing device configured to be connected to an electrical receptacle having an outlet face, said vapor dispensing device comprising a housing and a plug configured to be inserted into the outlet face, wherein the housing comprises a worst-case transverse loading point a perpendicular distance $d_L$ from the outlet face and a worst-case support point a distance $d_s$ from the plug, and wherein the distance $d_S$ is greater than the distance $d_L$;

a first device outlet electrically coupled to the plug; and a second device outlet electrically coupled to the plug.

2. The vapor dispensing device of claim 1 wherein the worst case support point is a point along a leading edge of the housing adjacent the front face and opposite the plug from the worst case transverse loading point.

3. The vapor dispensing device of claim 2 wherein the thickness of the housing is less than the shortest distance from the plug to the loading edge of the housing.

* * * * *